United States Patent
Cho et al.

(10) Patent No.: US 10,144,716 B2
(45) Date of Patent: Dec. 4, 2018

(54) POLYBENZOXAZINE PRECURSOR AND METHOD FOR PREPARING SAME

(71) Applicant: KOLON INDUSTRIES, INC., Gwacheon-si, Gyeonggi-do (KR)

(72) Inventors: Hee Jin Cho, Yongin-si (KR); Do Kyung Sung, Yongin-si (KR); Ki Hyun Park, Yongin-si (KR); Sang Hun Park, Yongin-si (KR)

(73) Assignee: KOLON INDUSTRIES, INC., Gwacheon-si (KR)

( * ) Notice: Subject to any disclaimer, the term of this patent is extended or adjusted under 35 U.S.C. 154(b) by 0 days.

(21) Appl. No.: 15/532,576

(22) PCT Filed: Dec. 7, 2015

(86) PCT No.: PCT/KR2015/013282
§ 371 (c)(1),
(2) Date: Jun. 2, 2017

(87) PCT Pub. No.: WO2016/089182
PCT Pub. Date: Jun. 9, 2016

(65) Prior Publication Data
US 2017/0327476 A1  Nov. 16, 2017

(30) Foreign Application Priority Data

Dec. 5, 2014 (KR) .................. 10-2014-0174117
Dec. 10, 2014 (KR) .................. 10-2014-0177622
Dec. 4, 2015 (KR) .................. 10-2015-0172225

(51) Int. Cl.
| | | |
|---|---|---|
| C07D 265/14 | (2006.01) | |
| C07D 265/12 | (2006.01) | |
| C07D 265/10 | (2006.01) | |
| C08G 8/10 | (2006.01) | |
| C08K 5/18 | (2006.01) | |
| C08G 61/12 | (2006.01) | |

(52) U.S. Cl.
CPC ............. *C07D 265/14* (2013.01); *C08G 8/10* (2013.01); *C08K 5/18* (2013.01); *C08G 61/122* (2013.01); *C08G 2261/135* (2013.01); *C08G 2261/148* (2013.01); *C08G 2261/3326* (2013.01); *C08G 2261/344* (2013.01); *C08G 2261/592* (2013.01); *C08G 2261/60* (2013.01); *C08G 2261/65* (2013.01); *C08G 2261/76* (2013.01)

(58) Field of Classification Search
CPC ... C07D 265/14; C07D 265/12; C07D 265/10
USPC ........................................................ 544/90
See application file for complete search history.

(56) References Cited

U.S. PATENT DOCUMENTS

| | | |
|---|---|---|
| 8,143,363 B2 | 3/2012 | Taden et al. |
| 9,120,763 B2 | 9/2015 | Wang et al. |
| 2011/0105680 A1 | 5/2011 | Taden et al. |
| 2014/0148597 A1 | 5/2014 | Wang et al. |

FOREIGN PATENT DOCUMENTS

| | | |
|---|---|---|
| CN | 1472205 A | 2/2004 |
| CN | 1284776 C | 11/2006 |
| EP | 1 901 312 A1 | 3/2008 |
| JP | 2003-064155 A | 3/2003 |
| JP | 2011-527356 A | 10/2011 |
| JP | 2014-521720 A | 8/2014 |
| TW | 201439096 A | 10/2014 |
| WO | 2011/116232 A1 | 9/2011 |

OTHER PUBLICATIONS

Zien Fu, et al., "Synthesis, Thermal Polymerization, and Properties of Benzoxazine Resins Containing Fluorenyl Moiety", Polymer Engineering and Science, 2012, pp. 2473-2481, vol. 52, No. 11.
Taiwanese Patent Office, Office Action of Taiwanese Patent Application No. 104140906, dated Jul. 11, 2016.
International Searching Authority, International Search Report of PCT/KR2015/013282, dated Jul. 11, 2016. [PCT/ISA/210].

*Primary Examiner* — Kahsay Habte
(74) *Attorney, Agent, or Firm* — Sughrue Mion, PLLC

(57) ABSTRACT

This invention relates to a polybenzoxazine precursor and a method of preparing the same, and more particularly, to a polybenzoxazine precursor which includes benzoxazine obtained by reacting a phenol novolak resin with an aldehyde compound and allylamine and diaminodiphenylmethane as an amine compound, and to a method of preparing the same. The polybenzoxazine precursor may serve to prepare a hardened material having excellent thermal and electrical characteristics and dimensional stability. Accordingly, the polybenzoxazine precursor may be available for use in a copper clad laminate, a semiconductor encapsulant, a printed circuit board, an adhesive, a paint, and a mold.

9 Claims, 4 Drawing Sheets

POLYBENZOXAZINE PRECURSOR AND METHOD FOR PREPARING SAME

CROSS REFERENCE TO RELATED APPLICATIONS

This application is a National Stage of International Application No. PCT/KR2015/013282 filed Dec. 7, 2015, claiming priorities based on Korean Patent Application Nos. 10-2014-0174117, filed Dec. 5, 2014, 10-2014-0177622, filed Dec. 10, 2014, and 10-2015-0172225, filed Dec. 4, 2015, the contents of all of which are incorporated herein by reference in their entirety.

TECHNICAL FIELD

The present invention relates to a polybenzoxazine precursor and a method of preparing the same.

BACKGROUND ART

Thermosetting resins such as phenol resins, melamine resins, epoxy resins, unsaturated polyester resins, and bismaleimide resins are based on thermosetting properties and are excellent in water resistance, chemical resistance, heat resistance, mechanical strength, and reliability. Accordingly, thermosetting resins have come to be widely used in various industrial fields.

However, phenol resins and melamine resins have drawbacks in that volatile byproducts are generated during hardening, epoxy resins and the unsaturated polyester resins have a drawback of poor flame retardancy, and bismaleimide resins have a drawback of very high cost.

In order to overcome the drawbacks, there has been studied polybenzoxazine obtained by performing a ring-opening polymerization reaction on a benzoxazine ring, which leads to thermosetting, without the generation of volatile matter, which is considered to be a problem.

To obtain a thermosetting resin having a benzoxazine ring in the molecular structure thereof, an oxazine ring is opened by heating and polymerization is performed without the generation of byproducts. Accordingly, the thermosetting resin having the benzoxazine ring is receiving attention as a thermosetting resin for use in an encapsulant, an impregnating agent, a laminate, an adhesive, a paint, a coating material, a friction material, FRP, and a molding material. Such a benzoxazine ring has a complex structure including benzene and oxazine rings.

Polybenzoxazines are hardened polymers having a high glass transition temperature (Tg), low permittivity, high tension, a low coefficient of thermal expansion, excellent elasticity, and low hygroscopicity, thus maintaining a balance between mechanical, electrical, and chemical properties.

Techniques for further enhancing the properties of benzoxazines have been continuously developed. For example, Korean Laid-Open Patent Application No. 10-2012-0058566 relates to a "polybenzoxazine composition", and discloses a method of preparing polybenzoxazine having favorable thermal stability, the method including heating a hardenable composition including a benzoxazine compound and a pentafluoroantimony acid catalyst at a sufficient temperature for a sufficient time to thus achieve polymerization.

Further, Korean Patent No. 10-0818254 relates to "a polybenzoxazine-based compound, an electrolyte membrane including the same, and a fuel cell using the same", and discloses a novel polybenzoxazine-based compound having improved acid trapping performance, mechanical and chemical stability, and ability to retain phosphoric acid at high temperatures, an electrolyte membrane using the same, and a method of preparing the same.

Meanwhile, a copper clad laminate (CCL) is a laminate with a thin copper foil on an insulating material. In accordance with the recent high performance and high integration of smart devices, a copper clad laminate used in a printed circuit board (PCB) is required to have excellent heat resistance and low permittivity. A resin is used as the base material of the copper clad laminate, and serves as an insulator in the printed circuit board. Permittivity must be low in order to form an excellent insulator. Permittivity refers to the degree of polarization of molecules in a nonconductor relative to an external electrical signal. The smaller the permittivity, the better the insulating performance. As the permittivity of the insulator is reduced during the operation of the printed circuit board, the processing speed of the signal is increased and transmission loss is reduced.

As an alternative to satisfy the requirements for heat resistance and low permittivity of the above-described copper clad laminate, the use of polybenzoxazine, which is a phenol-based hardening agent, has been emphasized. As described above, polybenzoxazine is a thermosetting polymer obtained by polymerizing a benzoxazine-based monomer while a ring is opened in a molecule of the monomer by heat. Polybenzoxazine can be self-hardened without byproducts, does not generate volatile materials, and is not changed in terms of volume during hardening, thus ensuring excellent dimensional stability. Further, polybenzoxazine is a highly heat-resistant polymer having a high glass transition temperature and decomposition of less than 1% at thermal decomposition temperatures of up to 350° C.

DISCLOSURE

Technical Problem

Accordingly, one embodiment of the present invention is intended to provide a polybenzoxazine precursor which is used to prepare a hardened material having improved thermal and electrical characteristics and dimensional stability compared to a conventional polybenzoxazine precursor.

Further, another embodiment of the present invention is intended to provide a method of preparing the polybenzoxazine precursor.

Further, another embodiment of the present invention is intended to provide a hardened material of the polybenzoxazine precursor.

Technical Solution

The embodiment provides:

a polybenzoxazine precursor including a benzoxazine compound represented by the following Chemical Formula 1 so that a content of the benzoxazine compound of the following Chemical Formula 1 where n1 is 0, n2 is 0, and m is 1 is 5 to 50%.

[Chemical Formula 1]

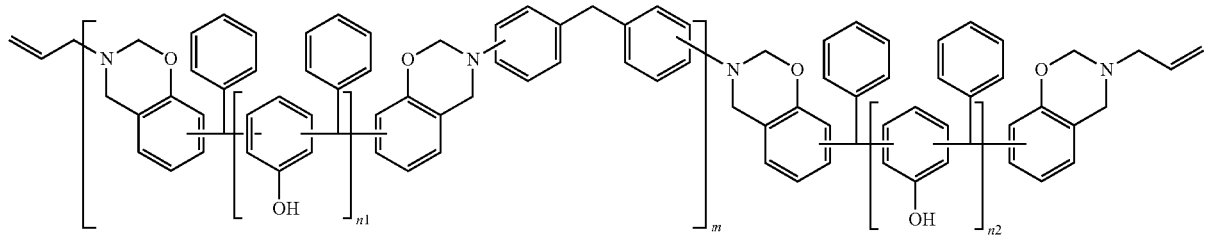

In Chemical Formula 1, n1 and n2 are identical or different and are each an integer of 0 to 2, and m is an integer of 1 to 6.

The precursor according to an embodiment may have a weight-average molecular weight of 1500 to 8000 g/mol and a glass transition temperature of 210° C. or higher.

The embodiment of the present invention provides a method of preparing a polybenzoxazine precursor, the method including reacting a phenol novolak resin with an aldehyde compound and allylamine and diaminodiphenylmethane as an amine compound.

The method according to a specific embodiment may include (1) reacting a phenol-based compound and the aldehyde compound in a presence of an acid catalyst to obtain the phenol novolak resin; and (2) reacting the obtained phenol novolak resin with the aldehyde compound and allylamine and diaminodiphenylmethane as the amine compound.

In the method according to the embodiments, the phenol novolak resin may be represented by the following Chemical Formula 2, and a component of Chemical Formula 2 where n is 0 may be included in a content of 65% or more.

[Chemical Formula 2]

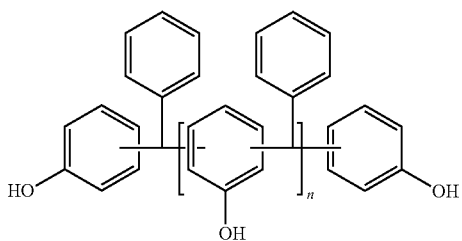

In Chemical Formula 2, n is an integer of 0 to 2.

In the embodiment, the aldehyde compound may be used in a content of 0.05 to 0.3 mol based on 1 mol of the phenol-based compound during step (1), and the aldehyde compound may be used in a content of 2 to 6 mol, allylamine may be used in a content of 0.5 to 1.5 mol, and diaminodiphenylmethane may be used in a content of 0.1 to 0.9 mol based on 1 mol of the phenol novolak resin during step (2).

The embodiment of the present invention provides a hardened material of the polybenzoxazine precursor according to the embodiments.

The embodiment of the present invention provides polybenzoxazine, obtained by opening an oxazine ring of a polybenzoxazine precursor, including a benzoxazine compound represented by Chemical Formula 1, to perform polymerization.

Another embodiment of the present invention provides a method of preparing polybenzoxazine, the method including hardening a polybenzoxazine precursor including a benzoxazine compound represented by Chemical Formula 1 at a temperature of 150 to 250° C.

Advantageous Effects

According to the embodiment of the present invention, a polybenzoxazine precursor may provide a hardened material having improved electrical and thermal characteristics and dimensional stability compared to a conventional polybenzoxazine precursor. Accordingly, the polybenzoxazine precursor may be available for use in a copper clad laminate, a semiconductor encapsulant, a printed circuit board, an adhesive, a paint, and a mold.

BEST MODE

Figure 1A:
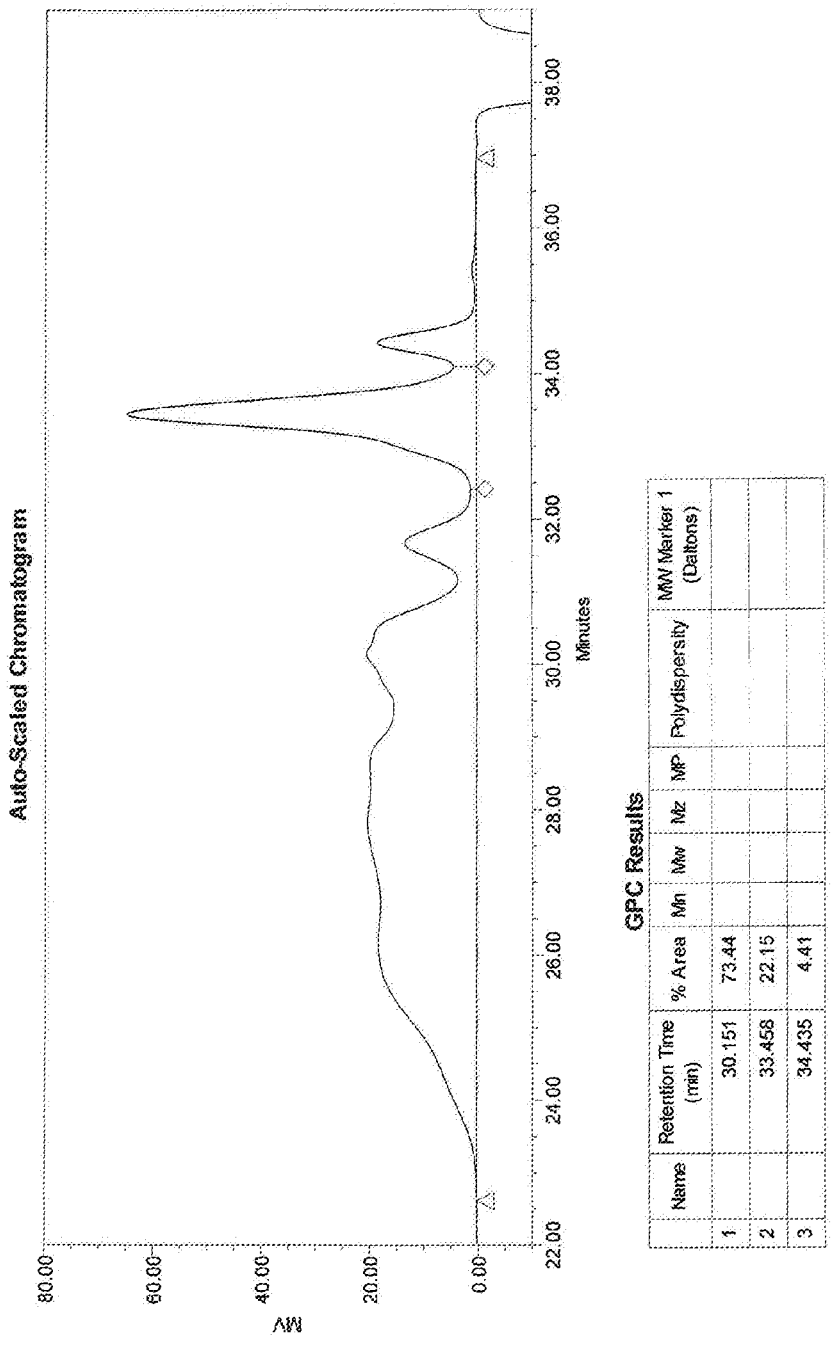
FIG. 1A and FIG. 1B show a GPC graph (FIG. 1A) and a $^1$H-NMR spectrum (FIG. 1B) of a polybenzoxazine precursor prepared in Example 1 of the embodiment, respectively.

Unless defined otherwise, all technical and scientific terms used in this specification have the same meanings as would be generally understood by those skilled in the related art to which the present invention pertains. In general, the nomenclature used herein is well known and commonly used in the art.

In the specification of the present application, when any portion "includes" any component, this means that the portion does not exclude other components but may further include other components unless otherwise stated.

The terms "about", "substantially", etc. as used herein are intended to be taken to mean an approximation to or at the numerical value when presenting the preparation and material tolerances inherent in the meanings mentioned, and also to prevent the disclosure content mentioning accurate or absolute numerical values from being maladapted by unauthorized intruders, thereby helping the understanding of the present invention.

An embodiment of the present invention provides a polybenzoxazine precursor which includes a benzoxazine compound represented by the following Chemical Formula 1 so that a content of the benzoxazine compound of the following Chemical Formula 1 where n1 is 0, n2 is 0, and m is 1 is 5 to 50%

[Chemical Formula 1]

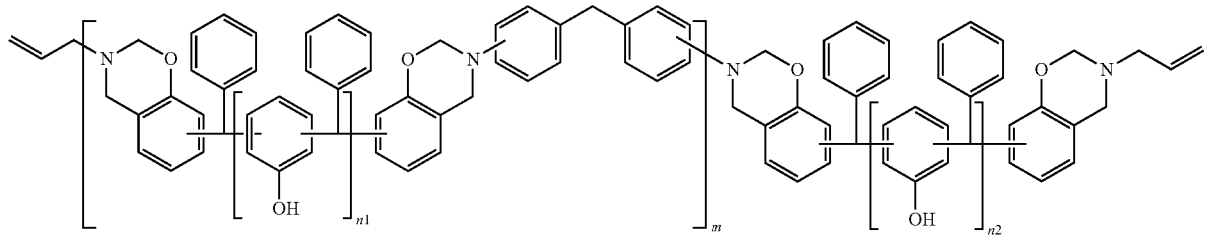

In Chemical Formula 1, n1 and n2 are identical or different and are each an integer of 0 to 2, and m is an integer of 1 to 6.

Throughout the specification, the term "polybenzoxazine precursor" means a compound or a compound group that serves as a precursor for forming a thermosetting resin which is obtained using a ring-opening reaction of an oxazine ring and which is called polybenzoxazine. The polybenzoxazine precursor is defined as including only benzoxazine-based monomers, as including oligomers including the monomers and an identical repeating-unit structure on a main chain thereof, or as including a combination including a portion of self-hardened materials obtained by polymerizing the monomers or the oligomers while opening the oxazine rings thereof.

Preferably, in order to improve electrical and thermal characteristics and dimensional stability, the polybenzoxazine precursor according to the embodiment of the present invention may include the benzoxazine compound, which is represented by Chemical Formula 1, so that the content of the compound is 5 to 50% based on the total precursor when n1 is 0, n2 is 0, and m is 1.

Throughout the present specification, the percentage (%) is based on the peak area ratio of gel permeation chromatography (GPC) (Waters: Waters707), and specifically means the peak area ratio between monomer and polymer components when the precursor includes the polymer. The rest is the same as above.

The polybenzoxazine precursor according to the embodiment of the present invention may include the compound of Chemical Formula 1 where n1 is 0, n2 is 0, and m is 1, and also compounds satisfying n1, n2, and m values in the range defined in Chemical Formula 1.

Preferably, the polybenzoxazine precursor may have a weight-average molecular weight of 1500 to 8000 g/mol in order to prevent delaying of hardening or crystallization during hardening, a reduction in workability due to the increased viscosity of the precursor or gelation of the precursor, and a reduction in compatibility with other resins.

The weight-average molecular weight may be defined by the converted value of the equivalent of polystyrene, determined using gel permeation chromatography (GPC).

The polybenzoxazine precursor according to the present invention may serve to provide a hardened material having thermal and electrical characteristics and dimensional stability that are improved compared to those of a M conventional polybenzoxazine precursor.

The polybenzoxazine precursor of the present invention may be manufactured using a phenol novolak resin, represented by the following Chemical Formula 2 as a raw material.

Chemical Formula 2

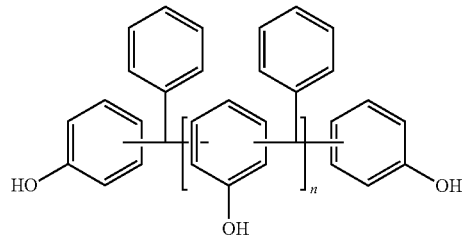

In Chemical Formula 2, n is an integer of 0 to 2.

Specifically, the phenol novolak resin, including 65% or more of the compound of Chemical Formula 2 where n is 0, may be used as the raw material to prepare the polybenzoxazine precursor.

More specifically, the polybenzoxazine precursor may be prepared using a method which includes (1) reacting a phenol-based compound and an aldehyde compound in the presence of an acid catalyst to obtain a phenol novolak resin, and (2) reacting the obtained phenol novolak resin with the aldehyde compound and monoamine and diamine compounds as an amine compound.

Still more specifically, the phenol-based compound and the aldehyde compound are reacted in the presence of the acid catalyst to obtain the phenol novolak resin including 65% or more (GPC area %) of the compound of Chemical Formula 2, where n is 0. Subsequently, the obtained phenol novolak resin undergoes a condensation reaction with the aldehyde compound and the monoamine and diamine compounds in the presence of a solvent, thus preparing the polybenzoxazine precursor containing benzoxazine in a maximum content of aromatics.

As described above, the phenol-based compound and the aldehyde compound may be reacted in the presence of the acid catalyst to obtain a phenol novolak resin including 65% or more (GPC area %) of the compound of Chemical Formula 2 where n is 0. When the content of the compound of Chemical Formula 2 where n is 0 is less than 65%, viscosity may be increased or gelation may occur due to the rapid reactivity and the high molecular weight of the raw material during the subsequent reaction of the preparation of benzoxazine.

Water and the solvent generated during the reaction may be removed using a known method such as distillation.

During step (1), the aldehyde compound may be added in a content of 0.05 to 0.3 mol, and preferably 0.1 to 0.2 mol, based on 1 mol of the phenol-based compound. When the aldehyde compound is added in a content of less than 0.05 mol based on 1 mol of the phenol-based compound, the yield may be rapidly reduced. When the content is more than 0.3 mol, the synthesized phenol novolak resin may include less than 65% of the component of Chemical Formula 2 where n is 0.

The phenol-based compound may be phenol or cresol.

Further, the aldehyde compound is not particularly limited, but specific examples thereof may include one or more selected from among the group consisting of benzaldehyde, anisaldehyde, 4-methylbenzaldehyde, 2-methoxybenzaldehyde, 4-methoxybenzaldehyde, 3,4-methylenedioxybenzaldehyde, 3,4-dimethoxy-benzaldehyde, and 3-isopropoxybenzaldehyde.

Examples of the acid catalyst used during step (1) may include one or more selected from among the group consisting of para-toluene sulfonic acid, methyl sulfonic acid, boron trifluoride, aluminum chloride, and sulfonic acid.

In step (2), the amine compound includes monoamine and diamine compounds in combination. Preferably, the monoamine may be allylamine and the diamine may be diaminodiphenylmethane in terms of reactivity and ease of preparation. The monoamine compound may be used in a content of 0.5 to 1.5 mol, and preferably 0.7 to 1.4 mol, based on 1 mol of the phenol novolak resin, the diamine compound may be added in a content of 0.1 to 0.9 mol, and preferably 0.2 to 0.6 mol, based on 1 mol of the phenol novolak resin, and the aldehyde compound may be added in a content of 2 to 6 mol, and preferably 3 to 5 mol, based on 1 mol of the phenol novolak resin.

When the monoamine compound is added in a content of less than 0.5 mol based on 1 mol of the phenol novolak resin, since a ring closure reaction does not occur, benzoxazine may be insufficiently reacted (a benzoxazine ring may be formed in an insufficient amount). When the content is more than 1.5 mol, thermal and electrical characteristics and dimensional stability are reduced duo to side reactions.

Further, when the diamine compound is added in a content of less than 0.1 mol based on 1 mol of the phenol novolak resin, the heat-resistant characteristic may be reduced due to the very small molecular weight thereof. When the content is more than 0.9 mol, the molecular weight may geometrically increase, thus reducing compatibility with resins or increasing the viscosity thereof.

Further, when the aldehyde compound is added in a content of less than 2 mol based on 1 mol of the phenol novolak resin, since the reaction with the amine compound insufficiently occurs, the oxazine ring may not be formed, and the heat-resistant characteristic may be reduced. When the content is more than 6 mol, an excessive amount of unreacted raw materials may remain in the product.

Examples of the solvent used in the reaction may include aromatic hydrocarbon-based solvents such as toluene, xylene, and trimethylbenzene; halogen-based solvents such as chloroform, dichloroform, and dichloromethane; and ether-based solvents such as THF and dioxane. Preferably, the content of the solvent is 25 to 100 parts by weight based on 100 parts by weight of the phenol novolak resin, the aldehyde compound, the monoamine compound, and the diamine compound.

During the preparation of the polybenzoxazine precursor, when the content of the solvent is very low, the viscosity of the reactant is increased, thus increasing alternating stress and reducing workability. When the content is very high, the cost of solvent removal after the reaction may be increased, which is uneconomic. Further, when the solvent is not appropriately selected and the mixing reaction is not performed as desired, the raw materials may not readily participate in the reaction, thus reducing the yield.

The prepared polybenzoxazine precursor may include 5 to 50% of the component of Chemical Formula 1, where n1 is 0, n2 is 0, and m is 1.

An embodiment of the present invention provides the hardened material of the polybenzoxazine precursor according to the above-described embodiments.

Throughout the specification, the term "hardened material" may mean not only the self-hardened material of the single polybenzoxazine precursor, but may also include the hardened material including the polybenzoxazine precursor resin and other resin-based compositions mixed therein.

In the embodiment of the present invention, there is provided polybenzoxazine obtained by opening an oxazine ring of a polybenzoxazine precursor, including a benzoxazine compound represented by Chemical Formula 1, to perform polymerization.

Particularly, polybenzoxazine may be obtained via a method of hardening the polybenzoxazine precursor including the benzoxazine compound represented by Chemical Formula 1 at a temperature of 150 to 250° C.

The hardening temperature of the polybenzoxazine precursor is preferably in the range of 150 to 250° C., and more preferably 190 to 220° C. When the temperature is lower than 150° C., the hardening time may be excessively long. When the temperature is higher than 250° C., impurities may be excessively oxidized or excess energy may be consumed during the process. It is more preferable that the temperature be 190 to 220° C. in view of processing time and energy efficiency. During the process of hardening benzoxazine, the oxazine ring of the benzoxazine compound represented by Chemical Formula 1 is opened, thus performing polymerization.

The hardened material that is obtained using the polybenzoxazine precursor according to the present invention may have excellent thermal and electrical characteristics and dimensional stability, thus being available for use in a copper clad laminate, a semiconductor encapsulant, a printed circuit board, an adhesive, a paint, and a mold.

Mode for Invention

A better understanding of the present invention may be obtained through the following Examples, which are set forth to illustrate, but are not to be construed as limiting, the present invention.

Example 1

1-1: Preparation of Polybenzoxazine Precursor 202.97 g of benzaldehyde and 1200.0 g of phenol were added at 40° C., and were reacted in the presence of a para-toluene sulfonic acid catalyst, which is an acid catalyst, at 130° C. for 5 hours, thus obtaining a phenol novolak resin containing 77.14% (GPC area %) of 4,4-(phenylmethylene)diphenol (the compound of Chemical Formula 2 where n is 0) and 22.86% of the compound of Chemical Formula 2, where n is 1 to 2, as the remains.

Next, 150 g (0.5286 mol) of the synthesized phenol novolak resin and 609.3 g of toluene were added to a 3 L three-neck flask subjected to purging using nitrogen. 30.83 g (0.540 mol) of allylamine and 52.40 g (0.2643 mol) of diaminodiphenylmethane were added thereto, and 158.75 g (2.114 mol) of a formaldehyde aqueous solution (40%) was then added. After the completion of addition, the temperature of the reaction solution was increased to 100° C. at a heating rate of 1.3° C./min, and the reaction solution was agitated for 5 hours. Subsequently, the temperature was increased to 120° C., and a solvent was completely removed under a pressure of 10 torr for 60 min, thus preparing 281 g of a polybenzoxazine precursor having a weight-average molecular weight of 2156 g/mol (including 22.15% of the component of Chemical Formula 1 where n1 is 0, n2 is 0, and m is 1). The yield was 99% (based on a theoretical yield according to the equivalence ratio of the reaction solution). The above-described % is the percentage of the peak area ratio (the ratio of monomer and polymer components) in gel permeation chromatography (GPC) (Waters: Waters707).

The molecular weight data of the polybenzoxazine precursor that was obtained were analyzed using the GPC, and the results are shown in FIG. 1A.

Figure 1B:
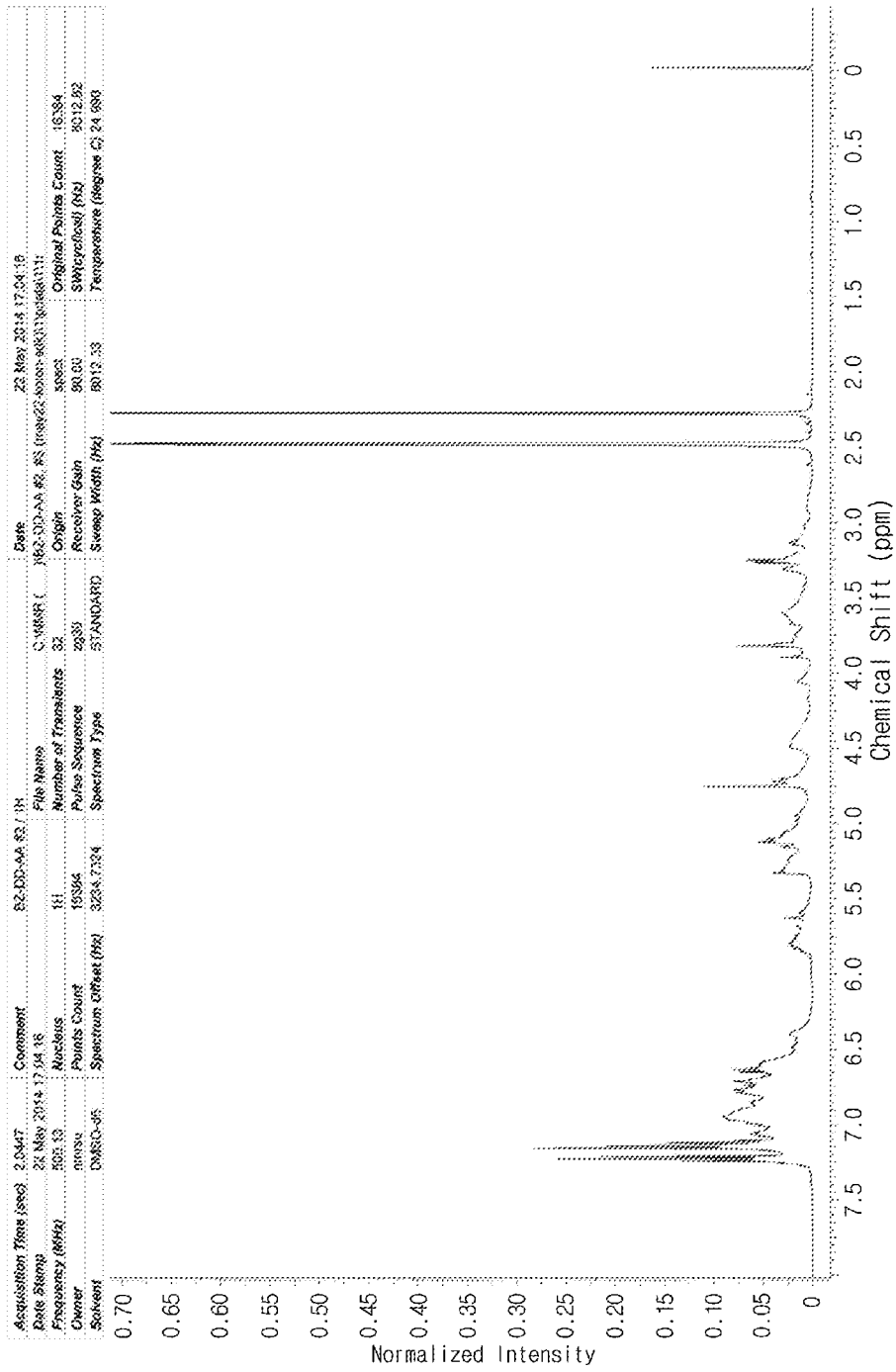

The structure of the polybenzoxazine precursor that W was obtained was confirmed using a nuclear magnetic resonance analysis method ($^1$H-NMR), and the result is shown in FIG. 1B. It could be confirmed that an —OH peak resulting from the raw material (the compound of Chemical Formula 2) was not observed around 8.0 to 9.0 ppm, but that a peak resulting from oxazine was formed in an wide region of 5.2 to 5.4 ppm, 4.3 to 4.6 ppm, 4.5 to 4.8 ppm, and 3.7 to 4.0 ppm.

An Avance 500, manufactured by Bruker Co., Ltd. was used as NMR equipment during NMR analysis.

1-2: Preparation of Hardened Material

The polybenzoxazine precursor obtained in Example 1-1 was added to an aluminum plate having a diameter of 30 mm and was self-hardened at 220° C. for 2 hours, thus preparing a sheet-type hardened material having a thickness of 1.5 mm.

Example 2

2-1: Preparation of Polybenzoxazine Precursor 197.33 g of benzaldehyde and 1250 g of phenol were added at 40° C., and were reacted in the presence of a para-toluene sulfonic acid catalyst, which is an acid catalyst, at 130° C. for 4 hours, thus obtaining a phenol novolak resin containing 75.27% (GPC area %) of 4,4-(phenylmethylene) diphenol (the compound of Chemical Formula 2 where n is 0) and 24.73% of the compound of Chemical Formula 2 where n is 1 to 2 as the remains.

Next, 150 g (0.5286 mol) of the synthesized phenol novolak resin and 609.3 g of toluene were added to a 3 L three-neck flask subjected to purging using nitrogen. 30.83 g (0.540 mol) of allylamine and 52.40 g (0.2643 mol) of diaminodiphenylmethane were added thereto, and 158.75 g (2.114 mol) of a formaldehyde aqueous solution (40%) was then added. After the completion of addition, the temperature of the reaction solution was increased to 100° C. at a heating rate of 1.3° C./min, and the reaction solution was agitated for 5 hours. Subsequently, the temperature was increased to 120° C., and a solvent was completely removed under pressure of 10 torr for 60 min, thus preparing 279 g of a polybenzoxazine precursor having a weight-average molecular weight of 2670 g/mol (including 16.46% of the component of Chemical Formula 1 where n1 was 0, n2 was 0, and m was 1). The yield was 99% (based on a theoretical yield according to the equivalence ratio of the reaction solution). The above-described % is the percentage of the peak area ratio (the ratio of monomer and polymer components) in gel permeation chromatography (GPC) (Waters: Waters707).

The molecular weight data of the polybenzoxazine precursor that was obtained were analyzed using GPC, and the result is shown in FIG. 1B.

The structure of the polybenzoxazine precursor that was obtained was confirmed using infrared spectroscopy. The result is shown in FIG. 2B, and a hydrogen atom peak of the oxazine ring (CH out of plane bending) was confirmed. A Spectrum 100, manufactured by PerkinElmer, Inc., was used as the infrared spectroscopy equipment.

Figure 2A:
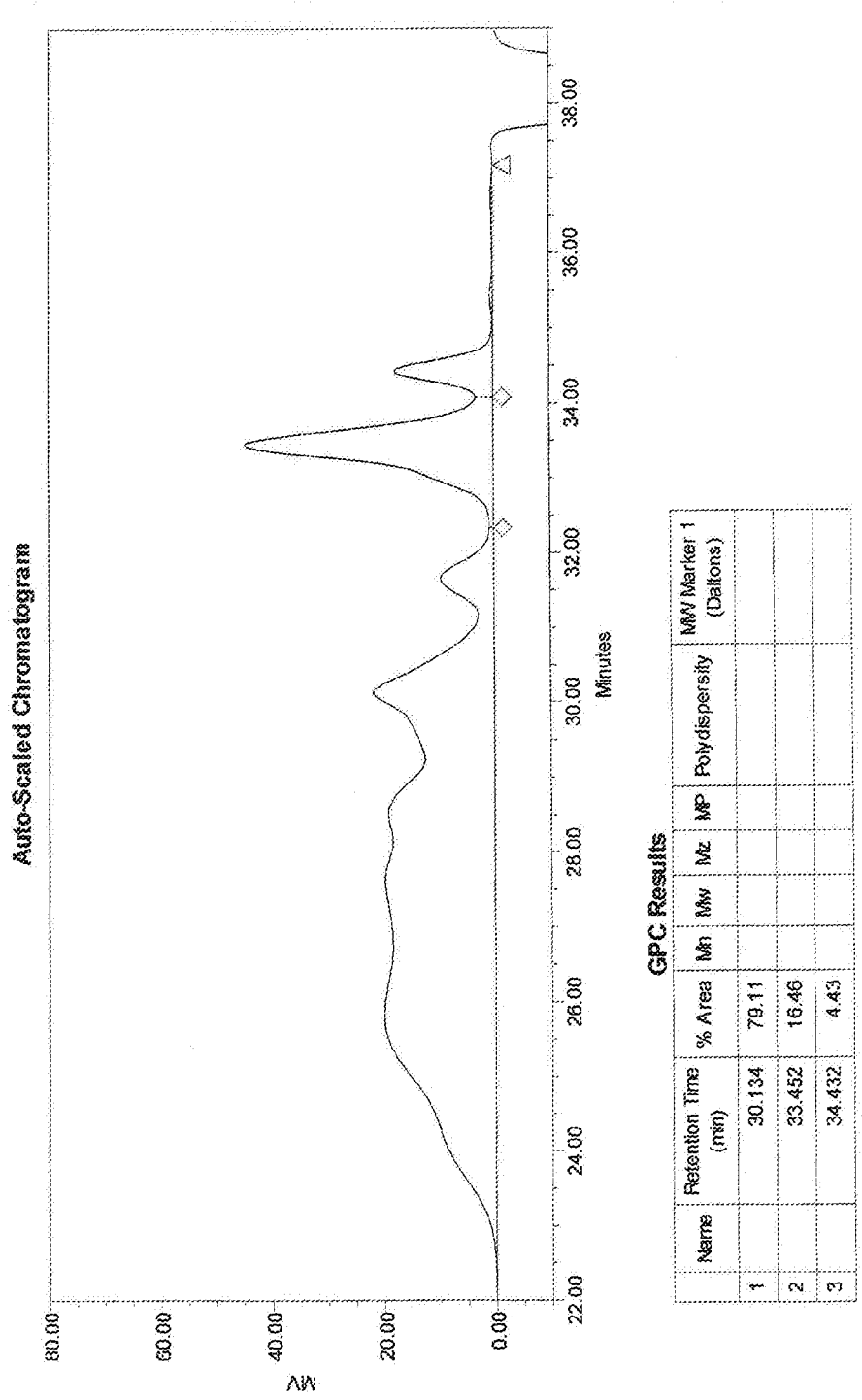
FIG. 2A shows a GPC graph of a polybenzoxazine precursor prepared in Example 2 of the embodiment.
Figure 2B:
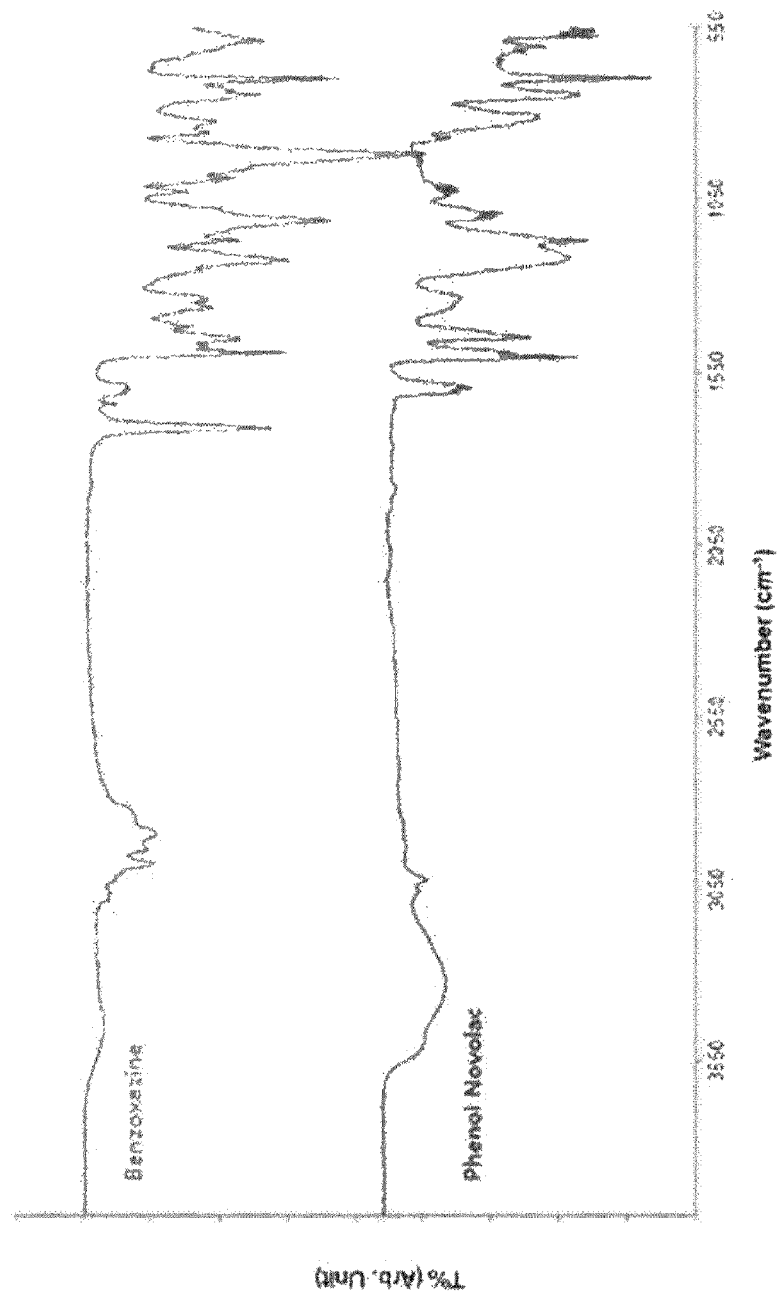
FIG. 2B shows infrared spectroscopy (IR) spectra of the polybenzoxazine precursor and a phenol novolak resin, which is a raw material.

From FIG. 2B, it could be confirmed that an —OH stretching peak resulting from an —OH group was not observed but that the characteristic peak of benzoxazine was observed (926 cm$^{-1}$ (the out-of-plane bending vibration of C—H) and 1234 cm$^{-1}$ (C—O—C asymmetric stretching modes)) in the case of the polybenzoxazine precursor designated by benzoxazine in FIG. 2, compared to the phenol novolak resin of Chemical Formula 2, which was a raw material.

2-2: Preparation of Hardened Material

The polybenzoxazine precursor obtained in Example 2-1 was added to an aluminum plate having a diameter of 30 mm and was self-hardened at 220° C. for 2 hours, thus preparing a sheet-type hardened material having a thickness of 1.5 mm.

Comparative Example 1

1-1: Preferation of Benzoxazine 484.2 g of toluene was added to a 3 L three-neck flask subjected to purging using nitrogen. 652.71 g (2.0 mol) of aniline, 800 g (1 mol) of bisphenol A, and 1052.35 g (4.0 mol) of a formaldehyde aqueous solution (40%) were added thereto. After the completion of the addition, the temperature of the reaction solution was increased to 100° C. at a heating rate of 1.3° C./min, and the reaction solution was agitated for 5 hours. Subsequently, the temperature was increased to 120° C., and a solvent was completely removed under pressure of 10 torr for 60 min, thus preparing 1500 g of a polybenzoxazine precursor having a weight-average molecular weight of 698 g/mol. The polybenzoxazine precursor that was obtained included 54.26% of a benzoxazine monomer, and a yield was 92% (based on a theoretical yield according to the equivalence ratio of the reaction solution). The above-described % is the percentage of the peak area ratio (the ratio of monomer and polymer components) in gel permeation chromatography (GPC) (Waters: Waters707).

1-2: Preparation of Hardened Material

The polybenzoxazine precursor obtained in Comparative Example 1-1 was added to an aluminum plate having a diameter of 30 mm, and was self-hardened at 220° C. for 3 hours, thus preparing a sheet-type hardened material having a thickness of 1.5 mm.

Comparative Example 2

2-1: Preparation of Benzoxazine 514.7 g of toluene was added to a 3 L three-neck flask subjected to purging using nitrogen. 744.18 g (2.0 mol) of aniline, 800 g (1 mol) of bisphenol F, and 1199.82 g (4.0 mol) of a formaldehyde aqueous solution (40%) were added thereto. After the completion of addition, the temperature of the reaction solution was increased to 100° C. at a heating rate of 1.3° C./min, and the reaction solution was agitated for 5 hours. Subsequently, the temperature was increased to 120° C., and a solvent was completely removed under pressure of 10 torr for 60 min, thus preparing 945 g of a polybenzoxazine precursor having a weight-average molecular weight of 1240 g/mol. The polybenzoxazine precursor that was obtained included 22.58% of a benzoxazine monomer, and a yield was 93% (based on a theoretical yield according to the equivalence ratio of the reaction solution). The above-described % is the percentage of the peak area ratio (the ratio of monomer and polymer components) in gel permeation chromatography (GPC) (Waters: Waters707).

2-2: Preparation of Hardened Material

The polybenzoxazine precursor obtained in Comparative Example 2-1 was added to an aluminum plate having a diameter of 30 mm, and was self-hardened at 220° C. for 2 hours, thus preparing a sheet-type hardened material having a thickness of 1.5 mm.

The glass transition temperature, the flame retardancy, the permittivity, and the molecular weight of the hardened materials prepared in Examples 1 and 2 and Comparative Examples 1 and 2 were measured using the following methods, and the results are described in the following Table 1.

<Measurement of Glass Transition Temperature (Tg)>

10 mg of the hardened materials prepared in Examples 1 and 2 and Comparative Examples 1 and 2 was measured for Tg using DMA (dynamic mechanical analysis).

Specifically, the measurement was performed using a TA Instruments DMA Q800 while being heated from 30° C. to 350° C. at a heating rate of 3° C./min.

<Measurement of Decomposition Temperature (Td 5)>

The hardened materials prepared in Examples 1 and 2 and Comparative Examples 1 and 2 were measured for Td 5 using a TGA measurement device and a TA Instruments TGA Q500 while being heated from 30° C. to 800° C. at a heating rate of 10° C./min in a nitrogen atmosphere.

<Measurement of Permittivity>

The permittivity (Dk) and the dielectric tangent (Df) of the hardened material were measured using an impedance analyzer (Agilent E4991A 1 MHz to 3 GHz), manufactured by Agilent company, under the following conditions.

Measured frequency: 1 GHz
Measured temperature: 25 to 27° C.
Measured humidity: 45 to 55%
Measured sample: thickness 1.5 mm (1.3 to 1.7 mm)

<Measurement of Molecular Weight>

The weight-average molecular weight (Mw) of polystyrene conversion was obtained via gel permeation chromatography (GPC) (Waters: Waters707). The polymer to be measured was dissolved in tetrahydrofuran so that the concentration was 4000 ppm, and the resulting solution was injected in an amount of 100 μl into the GPC. Tetrahydrofuran was used as the mobile phase of the GPC and was added at a flow rate of 1.0 mL/min, and analysis was performed at 35° C. Four columns of Waters HR-05, 1, 2, and 4E were connected in series. As for the detector, RI and PAD detectors were used in measurement at 35° C.

<Measurement of Coefficient of Thermal Expansion>

Measurement was performed using a TA Instruments TMA Q400 while being heated from 30° C. to 300° C. at a heating rate of 10° C./min. α1 is a coefficient of thermal expansion at room temperature to Tg and α2 is a coefficient of thermal expansion at Tg to 260° C.

TABLE 1

| Classi-fication | Mw (g/mol) | Tg (° C.) | Td 5 (° C.) | Coefficient of thermal expansion (α1/α2) | Permit-tivity (Dk) | Dielectric tangent (Df) |
|---|---|---|---|---|---|---|
| Example 1 | 2156 | 275.9 | 361.4 | 15.8/73.2 | 2.78 | 0.0047 |
| Example 2 | 2670 | 276.2 | 364.5 | 17.2/82.8 | 2.81 | 0.0049 |
| Comparative Example 1 | 698 | 198.7 | 314.6 | 51.08/3979 | 3.00 | 0.0100 |
| Comparative Example 2 | 1240 | 195.9 | 318.2 | 58.64/387.8 | 3.45 | 0.0150 |

As seen from Table 1, the Tg and Td values were higher in Examples 1 and 2 than in Comparative Examples 1 and 2. Accordingly, Examples 1 and 2 exhibited excellent thermal characteristics. Particularly, in Examples 1 and 2, the permittivity (Dk) and the dielectric tangent (Df) were low when measured, and accordingly the electrical characteristics were determined to be excellent. Further, the coefficient of thermal expansion was remarkably low, thus ensuring excellent dimensional stability.

It will be apparent to those skilled in the art that simple modifications or variations can be made in the present invention without departing from the spirit of the present invention.

The invention claimed is:

1. A polybenzoxazine precursor comprising:
a benzoxazine compound represented by the following Chemical Formula 1 so that a content of the benzoxazine compound of the following Chemical Formula 1 where n1 is 0, n2 is 0, and m is 1 is 5 to 50%:

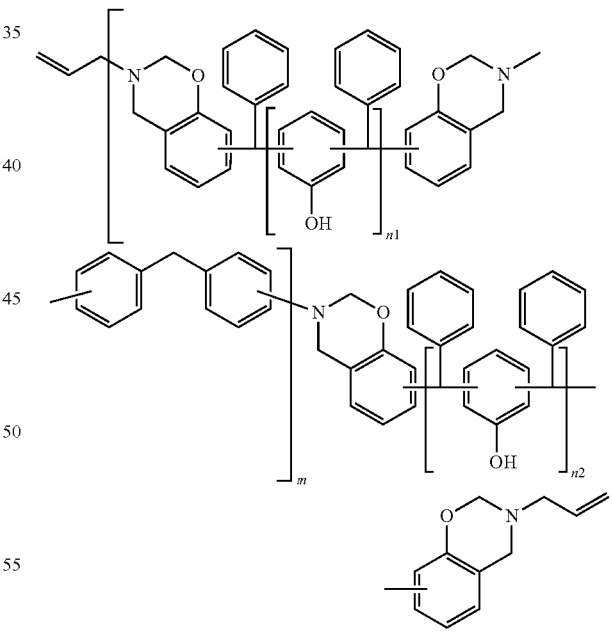

wherein n1 and n2 are identical or different and are each an integer of 0 to 2, and m is an integer of 1 to 6.

2. The polybenzoxazine precursor of claim 1, wherein the precursor has a weight-average molecular weight of 1500 to 8000 g/mol and a glass transition temperature of 210° C. or higher.

3. A method of preparing a polybenzoxazine precursor of claim 1, the method comprising:

reacting a phenol novolak resin with an aldehyde compound and allylamine and diaminodiphenylmethane as an amine compound,
wherein the phenol novolak resin is represented by the following Chemical Formula 2 and a component of Chemical Formula 2 where n is 0 is included in a content of 65% or more;

[Chemical Formula 2]

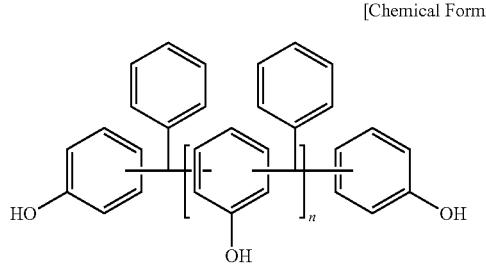

wherein n is an integer of 0 to 2.

4. The method of claim 3, wherein the method further comprises reacting a phenol-based compound and the aldehyde compound in a presence of an acid catalyst to obtain the phenol novolak resin.

5. The method of claim 4, wherein the phenol novolak resin includes the aldehyde compound in a content of 0.05 to 0.3 mol based on 1 mol of the phenol-based compound, and the aldehyde compound is used in a content of 2 to 6 mol, the allylamine is used in a content of 0.5 to 1.5 mol, and the diaminodiphenylmethane is used in a content of 0.1 to 0.9 mol based on 1 mol of the phenol novolak resin.

6. A hardened material prepared from the polybenzoxazine precursor of claim 1.

7. A polybenzoxazine, obtained by opening an oxazine ring of a polybenzoxazine precursor according to claim 1, to perform polymerization.

8. A method of preparing a polybenzoxazine, the method comprising:
hardening a polybenzoxazine precursor according to claim 1 at a temperature of 150 to 250° C.

9. The method of claim 4, wherein the phenol novolak resin is represented by the following Chemical Formula 2 and a component of Chemical Formula 2 where n is 0 is included in a content of 65% or more:

Chemical Formula 2

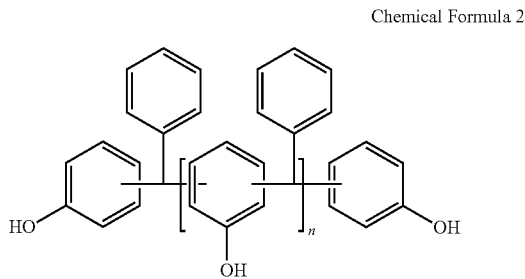

wherein n is an integer of 0 to 2.

* * * * *